(12) United States Patent
Yoshioka

(10) Patent No.: US 7,429,688 B2
(45) Date of Patent: Sep. 30, 2008

(54) DISPOSABLE DIAPER

(75) Inventor: Toshiyasu Yoshioka, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 1087 days.

(21) Appl. No.: 10/227,862

(22) Filed: Aug. 27, 2002

(65) Prior Publication Data

US 2003/0045845 A1 Mar. 6, 2003

(30) Foreign Application Priority Data

Aug. 31, 2001 (JP) ............................. 2001-263070

(51) Int. Cl.
*A61F 13/15* (2006.01)
*A61F 13/20* (2006.01)
*B32B 5/02* (2006.01)
*B32B 27/04* (2006.01)
*B32B 27/12* (2006.01)

(52) U.S. Cl. ...................... 604/361; 442/118

(58) Field of Classification Search ................. 604/361; 442/118; 106/31.59
See application file for complete search history.

(56) References Cited

U.S. PATENT DOCUMENTS

| | | | | |
|---|---|---|---|---|
| 3,675,654 A | * | 7/1972 | Baker et al. ................. | 604/361 |
| 5,766,212 A | * | 6/1998 | Jitoe et al. .................. | 604/361 |
| 5,776,308 A | * | 7/1998 | Sears et al. ................. | 162/158 |
| 6,297,424 B1 | * | 10/2001 | Olson et al. ................. | 604/361 |
| 6,632,974 B1 | * | 10/2003 | Suzuki et al. ............... | 604/369 |
| 6,730,819 B1 | * | 5/2004 | Pesce ......................... | 604/360 |
| 2002/0069988 A1 | * | 6/2002 | Yahiaoui et al. ............ | 162/123 |

FOREIGN PATENT DOCUMENTS

| | | |
|---|---|---|
| EP | 0 813 850 A2 | 12/1997 |
| JP | 1997-299401 A | 11/1997 |
| WO | WO 94/10958 | 5/1994 |
| WO | WO 00/65083 | 11/2000 |
| WO | WO 01/41691 | 6/2001 |
| WO | WO 0141691 A1 * | 6/2001 |

* cited by examiner

*Primary Examiner*—Tatyana Zalukaeva
*Assistant Examiner*—Melanie J Hand
(74) *Attorney, Agent, or Firm*—Lowe Hauptman Ham & Berner, LLP

(57) ABSTRACT

A disposable diaper includes a liquid-pervious topsheet, a liquid-impervious backsheet, a liquid-absorbent core interposed between these top- and backsheets, and an indicator by which it is perceptible from outside the backsheet whether urination has occurred or not. The indicator has a liquid-pervious intermediate sheet hydrophilically modified by coating of a hydrophobic fibrous nonwoven fabric with surfactant and a water-soluble coloring agent depicting a given figure which is perceptible from outside the backsheet. The intermediate sheet is interposed between the backsheet and the core and the coloring agent is applied on the surface of the intermediate sheet opposed to the backsheet.

20 Claims, 5 Drawing Sheets

DISPOSABLE DIAPER

BACKGROUND OF THE INVENTION

This invention relates to a disposable diaper provided with an indicator by which it is indicated visually from outside whether urination has occurred or not.

Japanese Patent Publication No. 1997-299401A discloses a disposable diaper comprising a liquid-pervious topsheet, a liquid-impervious backsheet and a liquid-absorbent core interposed between the top- and backsheets, defining a front waist region, a rear waist region and a crotch region extending between these waist regions, provided with an indicator which becomes visible and indicates an occurrence of urination from outside the backsheet when the front waist regions is wetted with urine.

The indicator comprises an ink layer which is disposed between the backsheet and the core and becomes visible when the ink layer is wetted with urine and an ink-covering layer which is disposed between the backsheet and the ink layer and put in close contact with the ink layer. The ink-covering layer contains a surfactant. The backsheet is made of breathable but liquid-impervious oriented plastic film containing fine particles of a titanium oxide, a calcium carbonate or a barium sulfate. This diaper is effective in that, when the indicator is wetted with urine, the surfactant contained in the ink-covering layer is dissolved in urine and the inner surface of the whitened backsheet is wetted with the urine and as a result the ink layer can be visually recognized through the backsheet.

Generally, it is unnecessary for a diaper that any third person other than a wearer's mother or a care personnel can detect whether urination has occurred or not. In the case of the diaper disclosed in the above-cited Publication, the ink layer becomes clearly visible upon urination, so urination is easily perceived by the third person. With this diaper, urination is pointed up by the third person and sometimes the diaper wearer's sense of pride may be injured.

SUMMARY OF THE INVENTION

It is an object of this invention to provide a disposable diaper enabling it to perceive from outside the diaper whether urination has occurred or not, without injuring the diaper wearer's sense of pride.

According to this invention, there is provided a disposable diaper comprising a liquid-pervious topsheet facing a wearer's body, a liquid-impervious backsheet facing away from the wearer's body and a liquid-absorbent core interposed between these top- and backsheets, defining a front waist region, a rear waist region and a crotch region extending between these waist regions wherein at least the front waist region out of the front and rear waist regions and the crotch region is provided with an indicator by which it is perceptible from outside the backsheet whether urination has occurred or not.

The disposable diaper further comprises the indicator composed of a liquid-pervious intermediate sheet hydrophilically modified by coating of a hydrophobic fibrous nonwoven fabric with surfactant and a water-soluble coloring agent depicting a given figure in color different from those of the backsheet and the intermediate sheet so that the figure is visible from outside the backsheet, wherein the intermediate sheet is interposed between the backsheet and the core and the coloring agent is applied on at least one of the surfaces of the backsheet and the intermediate sheet opposed to each other, and urine discharged on the diaper dissolves the surfactant and the coloring agent, then the surfactant and the coloring agent dissolved in urine permeate the intermediate sheet and is absorbed by the core, whereupon the figure substantially disappears and the intermediate sheet restores its initial hydrophobic property so as to prevent the coloring agent once absorbed by the core from flowing back toward the backsheet.

In one embodiment of this invention, the figure disappears within 30 seconds-2 minutes after urination has occurred.

In another embodiment of this invention, the intermediate sheet has a basis weight of 10-30 $g/m^2$ and a thickness of 0.1-3.0 mm.

In still another embodiment of this invention, the intermediate sheet is in close contact with the core.

In further another embodiment of this invention, the respective opposed surfaces of the backsheet and the intermediate sheet which are opposed to each other are in close contact with each other.

DETAILED DESCRIPTION OF THE PREFERRED EMBODIMENTS

Details of a pants-type disposable diaper according to this invention will be more fully understood from the description given hereunder in reference to the accompanying drawings.

Figure 1:
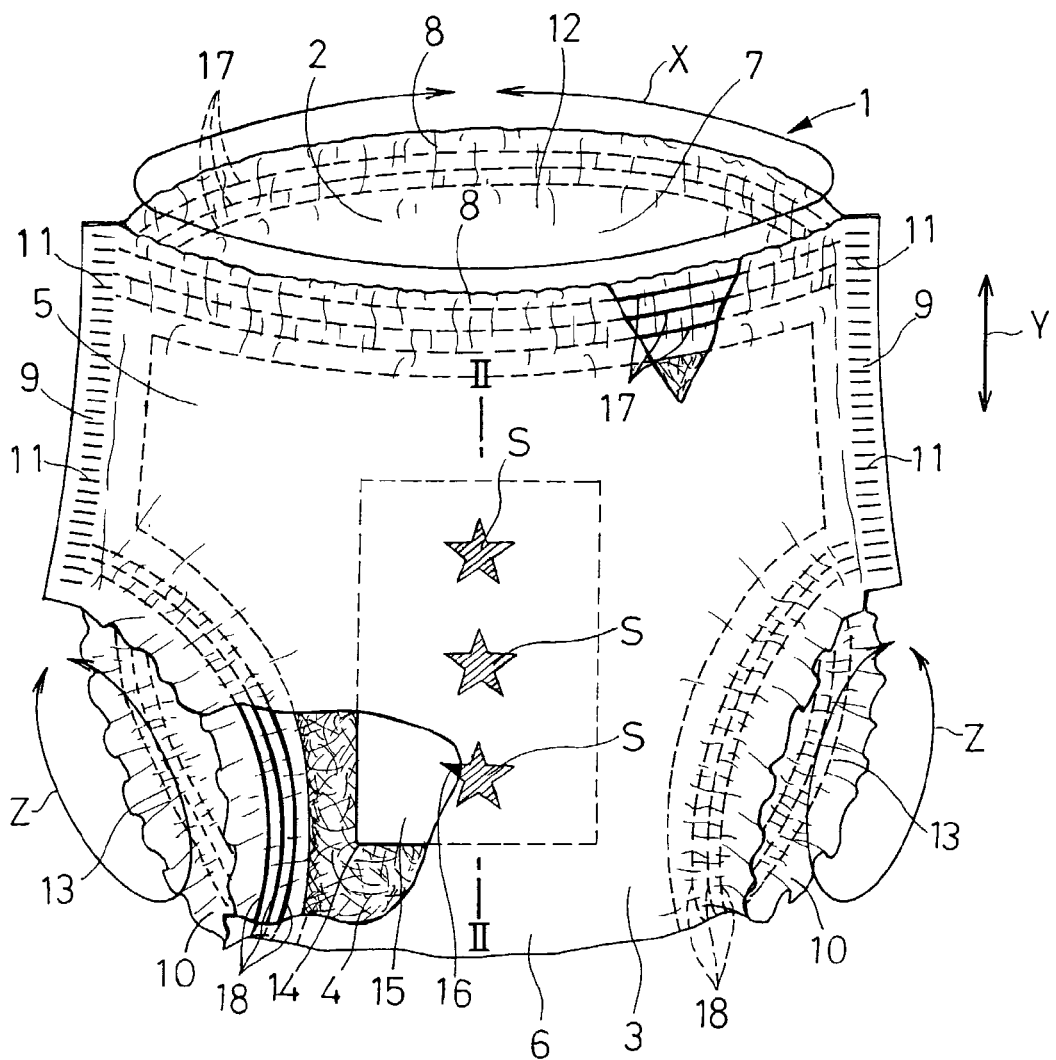
FIG. 1 is a partially cutaway perspective view showing a disposable diaper.
Figure 2:
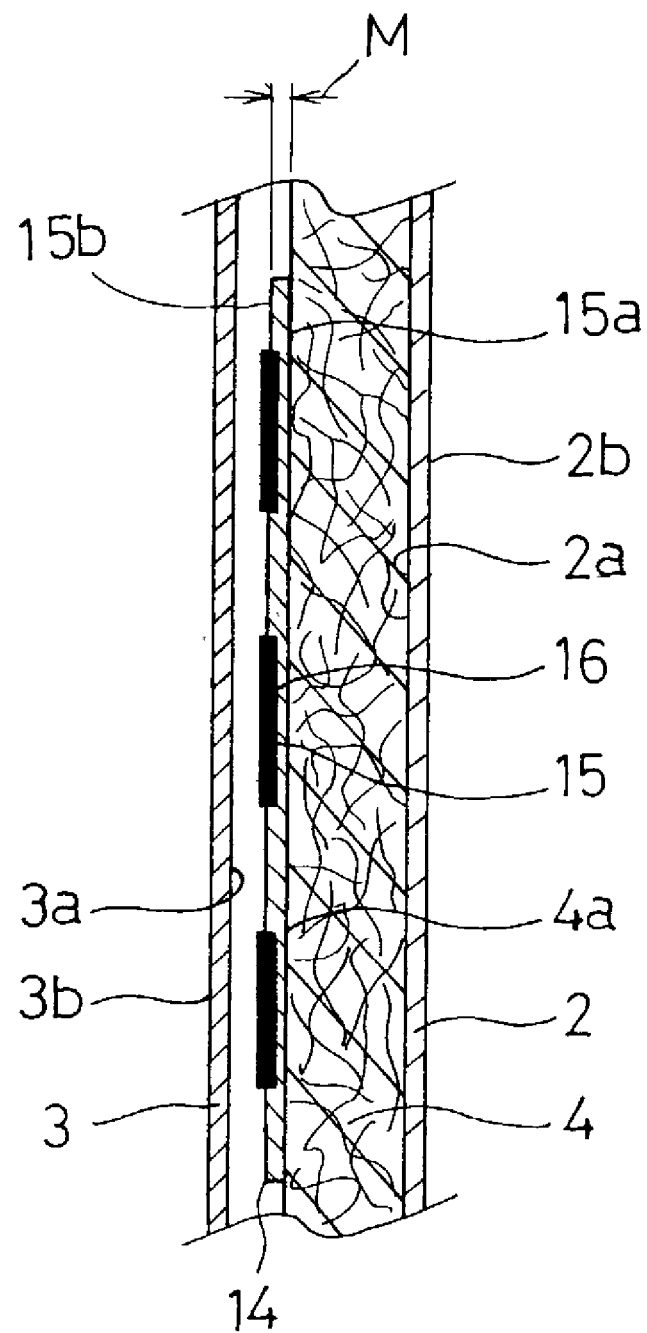
FIG. 2 is a sectional view taken along a line II-II in FIG. 1.

FIG. 1 is a partially cutaway perspective view showing a typical embodiment of a disposable diaper 1 according to this invention and FIG. 2 is a sectional view taken along a line II-II in FIG. 1. In FIG. 1, a waist-surrounding direction is indicated by an arrow X, a longitudinal direction is indicated by an arrow Y and a thigh-surrounding direction is indicated by an arrow Z. "Inner surfaces" 2a, 3a, 15a of top- and backsheets 2, 3 and an intermediate sheet 15, respectively, should be understood to mean the surfaces of these sheets facing a core 4 and "outer surfaces" 2b, 3b, 15b of these sheets 2, 3, 15, respectively should be understood to mean the surfaces of these sheets facing away from the core 4.

The diaper 1 comprises a liquid-pervious topsheet 2 facing a wearer's body, a liquid-impervious backsheet 3 facing away from the wearer's body and a liquid-absorbent core 4 interposed between these sheets 2, 3. The diaper 1 is composed of front and rear waist regions 5, 7 opposed to each other and a crotch region 6 extending between these front and rear waist regions 5, 7. The diaper 1 has waist-hole's peripheral portions 8 extending in the front and rear waist regions 5, 7 in the waist-surrounding direction, waist's side portions 9 extending in a longitudinal direction and leg-holes' peripheral portions 10 extending in the crotch region 6 in the thigh-surrounding direction.

In the diaper 1, the transversely opposite side edge portions 9 are overlaid and joined together on a plurality of heat-sealing lines 11 arranged intermittently in the longitudinal direction. In this manner, the diaper 1 is formed with a waist-hole 12 and a pair of leg-holes 13 lying below the waist-hole 12. The diaper 1 is provided in the front waist region 5 and the crotch region 6 with an indicator 14 by which it is perceptible from outside the backsheet 3 whether urination has occurred or not.

The waist-hole's peripheral portions 8 are provided with a plurality of waist-surrounding elastic members 17 which is extending in the waist-surrounding direction and bonded thereto in a stretched state. The leg-holes' peripheral portions 10 are provided with a plurality of thigh-surrounding elastic members 18 which is extending in the thigh-surrounding direction and bonded thereto in a stretched state. The waist-surrounding elastic members 17 and the thigh-surrounding elastic members 18 are interposed between the top- and backsheets 2, 3 and bonded to the inner surface 2a or 3a of at least one of these sheets 2, 3.

A stock material for the topsheet 2 may be selected a hydrophilic fibrous nonwoven fabric or a thermoplastic film having a plurality of fine pores. A stock material for the backsheet 3 may be selected from a group including of a hydrophobic fibrous nonwoven fabric, a breathable but liquid-impervious film obtained by orienting of a plastic film containing inorganic fine particles such as a titanium oxide, a calcium carbonate and a barium sulfate and a composite nonwoven fabric consisting of the hydrophobic fibrous nonwoven fabric and the breathable but liquid-impervious film laminated with each other. The backsheet 3 has a light transmittance of 30-80%. As the plastic film, a polyolefine- or a polyester-based thermoplastic resin film may be used. The top-and backsheets 2, 3 may be of white or milk-white color.

The core 4 are formed by a mixture of fluff pulp and super-absorbent polymer particles or a mixture of fluff pulp, super-absorbent polymer particles and thermoplastic synthetic resin fiber, in any case, compressed to a desired thickness. The core 4 is secured to the inner surface 2a of the topsheet 2. Preferably, the core 4 is entirely covered with a tissue paper in order to prevent the core 4 from getting out of shape and/or to prevent the polymer particles from falling off. The polymer particles may be selected from a group of materials including of a starch-based polymer, a cellulose-based polymer and a synthetic polymer.

The indicator 14 continuously extends so as to occupy a from the front waist region 5 toward the crotch region 6 and is attached to these regions 5, 6 in a middle zone thereof as viewed in the waist-surrounding direction. The indicator 14 comprises a liquid-pervious intermediate sheet 15 hydrophilically modified by coating of a hydrophobic fibrous nonwoven fabric with surfactant (not shown) and water-soluble coloring agent 16 of the color different from those of the backsheet 3 and the intermediate sheet 15 depicting a given figure which is visible from outside of the backsheet 3.

The intermediate sheet 15 is interposed between the backsheet 3 and core 4 in close contact with an outer surface 4a of the core 4 extending into the front waist region 5. The intermediate sheet 15 has its outer surface 15b (i.e., the surface opposed to the backsheet 3) is not joined to an inner surface 3a (the surface opposed to the outer surface 15b of the intermediate sheet 15) but has its inner surface 15a is joined together with the outer surface 4a of the core 4 by means of an intermittently applied adhesive (not shown). The intermediate sheet 15 is colored in white or milk-white. The figure S composed of three stars arranged in the longitudinal direction from the front waist region 5 toward the crotch region 6 are depicted on the intermediate sheet 15 in its middle zone as viewed in the waist-surrounding direction by the coloring agent 16. This coloring agent 16 is applied on the outer surface 15b of the intermediate sheet 15.

Figure 3:
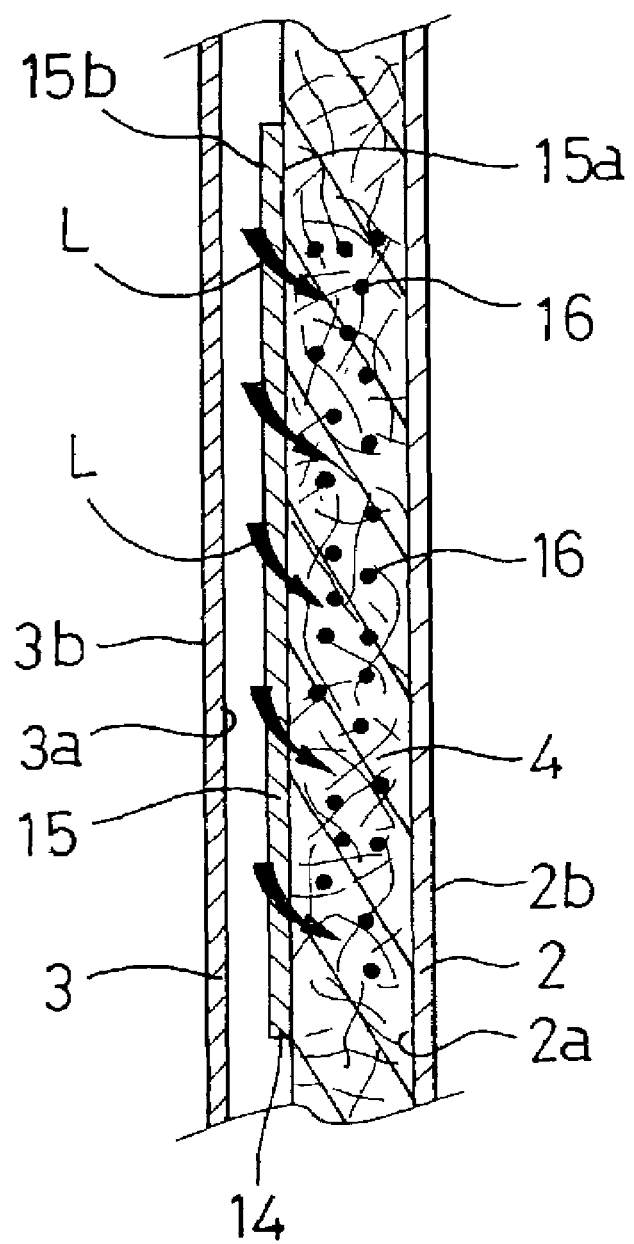
FIG. 3 is a diagram illustrating a manner in which urination causes variation in the indicator provided.

FIG. 3 is a diagram illustrating a manner in which urination causes variation of the indicator 14. Urine (not shown) discharged onto the diaper 1 exudes out from the core 4 to the indicator 14, on one route, and flows from the peripheral edge of the core 4 through the gap between the backsheet 3 and the core 4 to the indicator 14, on the other route. As the indicator 14 is wetted with urine, the surfactant applied to the intermediate sheet 15 and the coloring agent 16 are dissolved in urine and, as indicated by an arrow L, the surfactant and the coloring agent 16 which are dissolved in urine permeate the intermediate sheet 15 and then they are absorbed and retained together with urine by the core 4.

With this diaper 1, upon urination, the coloring agent 16 dissolved in urine is absorbed by the core 4 and, in consequence, the figure S depicted by the coloring agent 16 disappears. This feature enables it possible to be visible from outside the backsheet 3 whether urination has occurred or not. Compared to the diaper of the prior art in which the ink layer becomes obvious upon urination, in the case of the diaper 1 wherein the figure S disappears upon urination, it is difficult for a third person to perceive an occurrence of urination and point out that and therefore the wearer s sense of pride is not injured.

In the diaper 1, upon urination, the surfactant applied on the intermediate sheet 15 is dissolved in urine and then absorbed by the core 4. As a result, the intermediate sheet 15 restores its hydrophobic property and there is no possibility that the coloring agent 16 once absorbed by the core 4 might permeate the intermediate sheet 15 again and flow back toward the backsheet 3. With the diaper 1, even if the core 4 is colored by the coloring agent 16 which is absorbed thereby, the core 4 is concealed by the intermediate sheet 15 so that the color of the core 4 can not be visually recognized.

In the diaper 1, the figures S depicted with the coloring agent are arranged in the longitudinal direction in the front waist region 5 and the crotch region 6. With such a placement of the figures S, the figure S depicted in the front waist region 5 rapidly disappears when most of urine is discharged onto the front waist region 5 and the figures S depicted in the crotch region 6 rapidly disappears when most of urine is discharged onto the crotch region 6. Therefore it can be reliably perceived whether urination has occurred or not in the front waist region and/or the crotch region.

With the diaper 1, the figure S disappears within 30 Seconds-2 minutes after urination has occurred, and the intermediate sheet 15 has a basis weight of 10-30 g/m$^2$ and a thickness M of 0.1-3.0 mm. If the intermediate sheet 15 has the basis weight less than 10 g/m$^2$ and the thickness M less than 0.1 mm, it would be impossible for the intermediate sheet 15 to conceal the core 4 which has absorbed the coloring agent 16 and thereby has been colored. Consequently, it is likely that the color of the core 4 might be visually recognized from outside the backsheet 3. If the intermediate sheet 15 has the basis weight exceeding 30 g/m$^2$ and the thickness M exceeding 3.0 mm, a time until the figure S disappears would exceed 2 minutes because it takes a long time until the coloring agent 16 dissolved in urine permeates the intermediate sheet 15.

Figure 4:
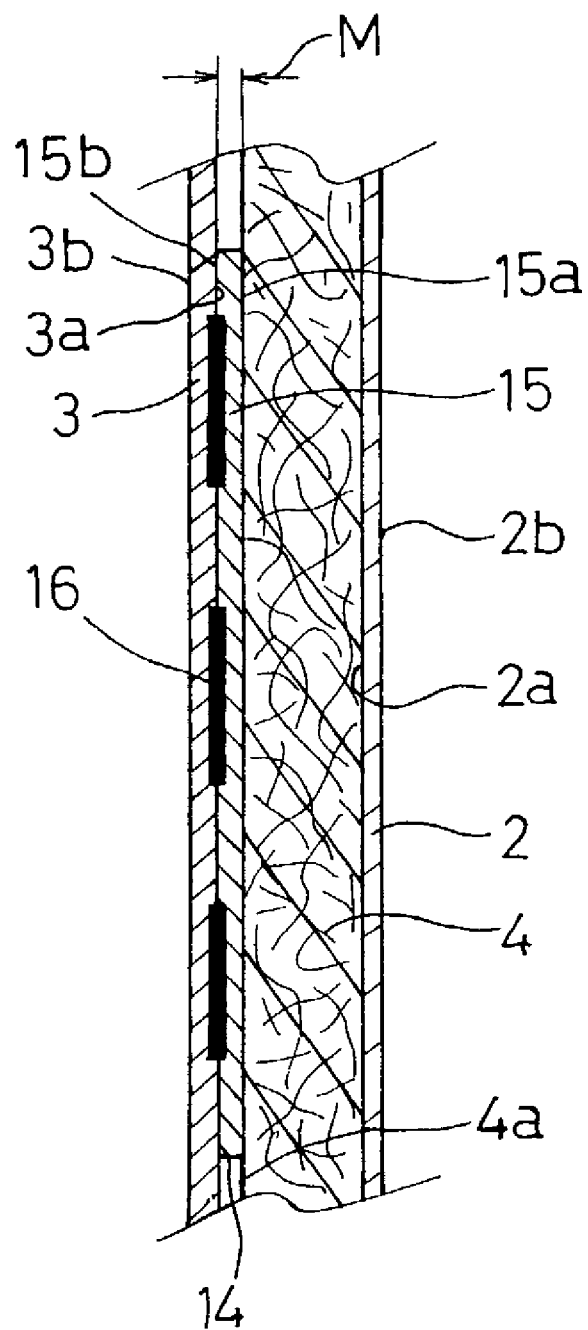
FIG. 4 is a sectional view similar to FIG. 2 showing another embodiment of this invention.
Figure 5:
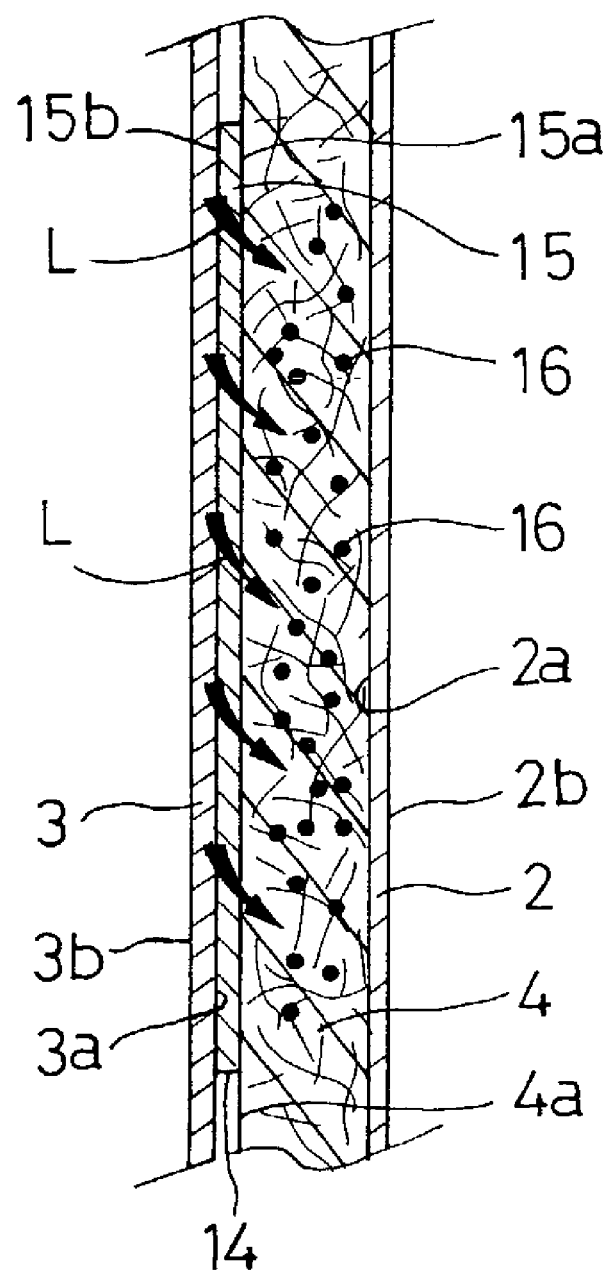
FIG. 5 is a diagram illustrating a manner in which urination causes variation in the indicator.

FIG. 4 is a cross-sectional view similar to FIG. 2 showing one preferred embodiment of this invention and FIG. 5 is a diagram illustrating a manner in which urination causes variation in the indicator 14. Referring to FIG. 4, the coloring agent 16 whose color differs from those of the backsheet 3 and the intermediate sheet 15 is applied on the inner surface 3a of the backsheet 3 and the outer surface 15b of the intermediate sheet 15 (the surfaces 3a, 15b are opposed to each other). The intermediate sheet 15 has its outer surface 15b (the surface opposed to the surface 3a) joined to the inner surface 3a of the backsheet 3 by means of an adhesive (not shown) intermittently applied thereon and its inner surface 15a joined to the outer surface 4a of the core 4 by means of an adhesive (not shown) intermittently applied thereon.

In this diaper 1, since the inner surface 3a of the backsheet 3 is in close contact with the outer surface 15b of the intermediate sheet 15, the coloring agent 16 dissolved in urine can more rapidly permeate the intermediate sheet 15 from the backsheet 3 and absorbed into the core 4 by contract with the embodiment such that the backsheet 3 and the intermediate sheet 15 are not in contact each other. Specifically, the figure S depicted with the coloring agent 16 disappears within 30 seconds-2 minutes after urination has occurred. The intermediate sheet 15 has the same basis weight and thickness M as those of the embodiment shown in FIG. 2.

In this diaper 1, peripheral portions of the top- and backsheets 2, 3 extending outward beyond the peripheral edge of the core 4 are overlaid and joined together. Joining of the top- and backsheets 2, 3, bonding of the elastic members 17, 18 to the top- and backsheets 2, 3 and joining of the core 4 to the topsheet 2 may be carried out using a hot melt adhesive or welding techniques such as a heat-sealing and a sonic sealing. For bonding using a hot melt adhesive, it may be applied on the top- and backsheets 2, 3 in an appropriate pattern such as spiral pattern or spray pattern.

In this diaper 1, the indicator 14 may be attached to at least one of the front and rear waist regions 5, 7 and the crotch region 6. The intermediate sheet 15 preferably has a size at least twice the figure S depicted with the coloring agent 16. The figure S depicted with the coloring agent 16 preferably lies substantially in the middle of the intermediate sheet 15. It is also possible to apply the coloring agent 16 on the inner surface 3a of the backsheet 3.

The figure S depicted with the coloring agent 16 is not specified and the stars as shown may be replaced by a geometric pattern such as a circle, a triangle, a square or a rhombus, or a graphic of suitable character or letters. The number of the components constituting the figure S is not limited to three as shown but may be one, two, three or more.

The surfactant may be ionic or nonionic. The ionic surfactant may be selected from a group consisting of various anionic surfactants such as a carboxylate, a sulfate ester, a sulfonate and a phosphate ester, and various cationic surfactants such as a monoalkylamine hydrochloride, a dialkylamine hydrochloride and a trialkylamine hydrochloride, and a various ampholytic surfactants such as an amino acid type and ammonium type surfactant. The nonionic surfactant may be selected from a group consisting of a polyoxyethylene type and a polyvalent alcohol type surfactant.

As the water-soluble coloring agent 16, a food dye dissolved in water or alcohol or a water-soluble ink may be used. Examples of such a coloring agent include aqueous solution of Edible Red No. 105 (rose Bengal) dissolved in water or alcohol (solubility in water: 36.25 g/100 ml (26° C.), solubility in alcohol: 7.53 g/100 ml (26° C.)), Edible Green No. 3 (Fast Green FCF) dissolved in water or alcohol (solubility in water: 24.9 g/100 ml (21° C.), solubility in alcohol: 6.8 g/100 ml (21° C.)) and Edible Blue No. 1 (Brilliant Blue FCF) dissolved in water or alcohol (solubility in water: 18.7 g/100 ml (21° C.), solubility in alcohol: 9.0 g/100 ml (21° C.)). A color of the coloring agent 16 is not specified so far as the color differs from those of the backsheet 3 and the intermediate sheet 15.

An adhesive used for joining of the intermediate sheet 15 is not specified but it is preferred to use a hydrophilic natural polymeric adhesive such as a starch or a hide glue, or a water-soluble synthetic polymeric adhesive such as a polyvinyl alcohol or a polyvinyl pyrrolidone. It is also possible to use a hot melt adhesive for this purpose.

Nonwoven fabric as a stock material for the top- and backsheets 2, 3 and the intermediate sheet 15 may be selected from a group including products obtained by spun lacing, needle punching, melt blowing, thermal bonding, spun bonding, chemical bonding and air-through processes. Component fibers of the nonwoven fabric may be selected from a group including polyolefine-, polyester- and polyamide-based fibers and core-sheath-type and side-by-side-type conjugated fibers of polyethylene/polypropylene and polyethylene/polyester.

This invention is applicable not only to the pants-type diaper 1 having the front and rear waist regions 5, 7 previously connected to each other as has been described above but also to so-called open-type diaper of which the front and rear waist regions are connected to each other immediately before the diaper is actually used.

With the disposable diaper according to this invention, upon urination, the coloring agent dissolved in urine is absorbed by the core and consequently the figure depicted with this coloring agent disappears so that urination can be visually perceived from outside the backsheet. The figure disappears after urination has occurred, so it is difficult for a third person to perceive and to point out occurrence of urination. In this way, there is no anxiety that the wearer's sense of pride might be injured.

In this diaper, as the surfactant applied on the intermediate sheet is absorbed by the core, the intermediate sheet restores its initial hydrophobic property and therefore the coloring agent which is dissolved in urine and absorbed by the core never permeate the intermediate sheet again and flow back toward the backsheet. Even if the core has been colored by the coloring agent absorbed therein, the intermediate sheet conceals the core so that the color of the core be invisible from outside the backsheet.

What is claimed is:

1. A disposable diaper comprising a liquid-pervious topsheet facing a wearer's body, a liquid-impervious backsheet facing away from the wearer's body and a liquid-absorbent core interposed between said top- and backsheets so as to define a front waist region, a rear waist region and a crotch region extending between said waist regions wherein at least one of said front and rear waist regions and said crotch region is provided with an indicator by which it is perceptible from outside said backsheet whether urination has occurred or not, said disposable diaper further comprising; said indicator being composed of an intermediate sheet comprising a hydrophobic fibrous nonwoven fabric, wherein the nonwoven fabric has a coating thereon comprising a surfactant that hydrophilically modifies said intermediate sheet upon application to the intermediate sheet, and a water-soluble coloring agent depicting a given figure in color different from those of said backsheet and said intermediate sheet; said figure being visible from outside said backsheet, wherein said intermediate sheet is interposed between said backsheet and said core and said coloring agent is applied on at least one of opposed surfaces of said backsheet and said intermediate sheet which are opposed to each other; and urine discharged on said diaper dissolves said surfactant and said coloring agent, said surfactant and said coloring agent dissolved by said urine permeating said intermediate sheet and being absorbed by said core, whereupon said figure substantially disappears and said intermediate sheet restores its initial hydrophobic property so as to prevent said coloring agent once absorbed by said core from flowing back toward said backsheet.

2. The diaper according to claim 1, wherein said figure disappears within 30 seconds-2 minutes after urination has occurred.

3. The diaper according to claim 1, wherein said intermediate sheet has a basis weight of 10-30 g/m² and a thickness of 0.1-3.0 mm.

4. The diaper according to claim 1, wherein said intermediate sheet is in close contact with said core.

5. The diaper according to claim 1, wherein the respective opposed surfaces of said backsheet and said intermediate sheet which are opposed to each other are in close contact with each other.

6. The diaper according to claim 1, wherein the surfactant is an ionic surfactant.

7. The diaper according to claim 6, wherein the ionic surfactant is an anionic surfactant selected from the group consisting of a carboxylate, a sulfate ester, a sulfonate and a phosphate ester.

8. The diaper according to claim 6, wherein the ionic surfactant is a cationic surfactant selected from the group consisting of a monoalkylaniine hydrochloride, a dialkylamine hydrochloride and a trialkylamine hydrochloride.

9. The diaper according to claim 6, wherein the ionic surfactant is an ampholytic surfactant selected from the group consisting of amino acid type and ammonium type surfactants.

10. The diaper according to claim 1, further comprising a gap between said backsheet and said intermediate sheet allowing urine to flow through said gap between the backsheet and the intermediate sheet and to come into contact with and dissolve the surfactant and the coloring agent.

11. A disposable diaper, comprising
a liquid-pervious topsheet, a liquid-impervious backsheet and a liquid-absorbent core interposed between said topsheet and backsheet;
an intermediate sheet disposed between the backsheet and the absorbent core, said intermediate sheet having an initial hydrophobic property and being rendered liquid pervious by a surfactant; and
an urine indicator comprising a water-soluble coloring agent applied on at least one of opposing surfaces of said intermediate sheet and said backsheet;
wherein
said indicator, when not wetted with urine, is visible from an outside of said diaper through said backsheet and visually differentiable from said backsheet and said intermediate sheet;
said coloring agent and said surfactant are dissolvable by urine and absorbable by said core, causing said indicator to disappear and restoring the initial hydrophobic property of said intermediate sheet; and
said coloring agent dissolved and absorbed in said core is concealed and visually unrecognizable from the outside through said intermediate sheet having the restored initial hydrophobic property.

12. The diaper according to claim 11, wherein said coloring agent is applied in an amount sufficient to be completely dissolved within 30 seconds-2 minutes after contact with urine.

13. The diaper according to claim 11, wherein said backsheet has a light transmittance of 30-80%.

14. The diaper according to claim 11, wherein said coloring agent is applied on an outer surface of said intermediate sheet and spaced from an inner surface of said backsheet by said gap.

15. The diaper according to claim 11, wherein said coloring agent comprises a water-soluble food dye.

16. The diaper according to claim 11, wherein the surfactant is an ionic surfactant.

17. The diaper according to claim 16, wherein the ionic surfactant is an anionic surfactant selected from the group consisting of a carboxylate, a sulfate ester, a sulfonate and a phosphate ester.

18. The diaper according to claim 16, wherein the ionic surfactant is a cationic surfactant selected from the group consisting of a monoalkylamine hydrochloride, a dialkylamine hydrochloride and a trialkylamine hydrochloride.

19. The diaper according to claim 16, wherein the ionic surfactant is an ampholytic surfactant selected from the group consisting of amino acid type and ammonium type surfactants.

20. The diaper according to claim 14, further comprising a gap between said backsheet and said intermediate sheet allowing urine to flow through said gap between the backsheet and the intermediate sheet and to come into contact with and dissolve the surfactant and the coloring agent.

* * * * *